(12) United States Patent
Davies et al.

(10) Patent No.: US 9,089,649 B2
(45) Date of Patent: Jul. 28, 2015

(54) MEDICATED MODULE FOR A DRUG DELIVERY DEVICE

(75) Inventors: James Alexander Davies, Warwickshire (GB); Steven Wimpenny, Leamington Spa (GB); Daniel Thomas De Sausmarez Lintell, Rugby (GB); Malcolm Stanley Boyd, Wellsbourne (GB); Naceur Rekaya, Leamington Spa (GB); Simon Lewis Bilton, Leamington Spa (GB); John David Cross, Long Buckby (GB); David Moore, Elmesthorpe (GB); Graham Jay, Frankfurt (DE); Ross Douglas MacArthur, Sandbach (GB); Michael James David Heald, Maidenhead (GB); Christopher James Smith, Holmes Chapel (GB)

(73) Assignee: Sanofi-Aventis Detuschland GmbH, Frankfurt am Main (DE)

( * ) Notice: Subject to any disclaimer, the term of this patent is extended or adjusted under 35 U.S.C. 154(b) by 486 days.

(21) Appl. No.: 13/375,994

(22) PCT Filed: Jun. 1, 2010

(86) PCT No.: PCT/EP2010/057578
§ 371 (c)(1),
(2), (4) Date: Feb. 13, 2012

(87) PCT Pub. No.: WO2010/139670
PCT Pub. Date: Dec. 9, 2010

(65) Prior Publication Data
US 2012/0130346 A1 May 24, 2012

Related U.S. Application Data

(60) Provisional application No. 61/183,455, filed on Jun. 2, 2009.

(30) Foreign Application Priority Data

Jul. 25, 2009 (EP) .................................... 09009660

(51) Int. Cl.
*A61M 5/31* (2006.01)
*A61M 5/32* (2006.01)
(Continued)

(52) U.S. Cl.
CPC ........... *A61M 5/2448* (2013.01); *A61M 5/2466* (2013.01); *A61M 5/32* (2013.01);
(Continued)

(58) Field of Classification Search
CPC ............... A61M 2005/247; A61M 2005/2474; A61M 2005/1787; A61M 5/2448; A61M 5/284; A61M 5/285; A61M 5/288; A61M 5/2066
See application file for complete search history.

(56) References Cited

U.S. PATENT DOCUMENTS 2,132,763 A 10/1938 Smith
3,563,240 A 2/1971 Silver
(Continued)

FOREIGN PATENT DOCUMENTS

CN 1507360 A 6/2004
CN 1509192 A 6/2004
(Continued)

OTHER PUBLICATIONS

English Translation of Japanese Patent Application No. 2012-513583 Notification of Reasons for Refusal Dated May 20, 2014.
(Continued)

*Primary Examiner* — Nicholas Lucchesi
*Assistant Examiner* — Justin L Zamory
(74) *Attorney, Agent, or Firm* — McDonnell Boehnen Hulbert & Berghoff LLP

(57) ABSTRACT

A medicated module (4) for an injection system to co-deliver at least two medicaments (1, 2) is disclosed where a primary delivery device (7) containing a primary medicament (1) accepts a medicated module (4) containing a single dose of a secondary medicament (2) and where both medicaments (1, 2) are delivered through a single hollow needle (3, 16, 21, 31).

14 Claims, 4 Drawing Sheets

(51) Int. Cl.
   *A61M 5/24* (2006.01)
   *A61M 5/315* (2006.01)
   *A61M 5/34* (2006.01)
   *A61M 5/178* (2006.01)

(52) U.S. Cl.
   CPC ........ *A61M 5/3294* (2013.01); *A61M 5/31525* (2013.01); *A61M 5/31556* (2013.01); *A61M 5/347* (2013.01); *A61M 2005/1787* (2013.01); *A61M 2206/20* (2013.01)

(56) References Cited

U.S. PATENT DOCUMENTS

| | | | |
|---|---|---|---|
| 3,908,654 A | | 9/1975 | Lhoest et al. |
| 5,281,198 A | * | 1/1994 | Haber et al. .................... 604/86 |
| 5,599,312 A | | 2/1997 | Higashikawa |
| 6,562,002 B1 | | 5/2003 | Taylor |
| 2006/0229562 A1 | | 10/2006 | Marsh et al. |
| 2008/0039795 A1 | * | 2/2008 | Slate et al. .................... 604/136 |
| 2008/0114304 A1 | | 5/2008 | Nalesso et al. |
| 2008/0281271 A1 | | 11/2008 | Griffiths et al. |
| 2009/0093792 A1 | | 4/2009 | Gross et al. |

FOREIGN PATENT DOCUMENTS

| | | |
|---|---|---|
| EP | 0298585 A1 | 1/1989 |
| EP | 0401822 A2 | 12/1990 |
| WO | 8802265 A1 | 4/1988 |
| WO | 0066214 A1 | 11/2000 |
| WO | 0189613 A1 | 11/2001 |
| WO | 02072173 A2 | 9/2002 |
| WO | 2008140737 A2 | 11/2008 |

OTHER PUBLICATIONS

English translation of the Text of the Second Office Action of Chinese Patent Application No. 201080024071.5.

First Office Action issued by the Chinese Patent Office for Chinese Patent Application No. 201080024071.5 dated Feb. 7, 2013.

English Translation of the First Office Action issued by the Chinese Patent Office for Chinese Patent Application No. 201080024071.5 dated Feb. 7, 2013.

Australian Government IP Australia, Patent Examination Report No. 1 dated Feb. 13, 2014.

* cited by examiner

MEDICATED MODULE FOR A DRUG DELIVERY DEVICE

CROSS REFERENCE TO RELATED APPLICATIONS

The present application is a 35 U.S.C. 371 National Application of PCT/EP2010/057578 filed Jun. 1, 2010, which claims priority to U.S. Provisional Patent Application No. 61/183,455 filed Jun. 2, 2009 and European Patent Application No. 09009660.3 filed Jul. 25, 2009, the entire contents of which are incorporated entirely herein by reference.

FIELD OF THE PRESENT PATENT APPLICATION

According to specific embodiments, this disclosure relates to medical devices and methods of delivering at least two drug agents from separate reservoirs using devices having only a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Our invention may be of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two or more active medicaments or "agents" simultaneously. The two or more active agents may interact with each other during the long-term, shelf life storage of the formulation. A formulation comprising at least two active agents will preferably be understood as pre-mix/premix medicament or pre-mixed/pre-mixed formulation, in the context of this disclosure. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple for the user to perform. In specific embodiments, our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Moreover, in specific embodiments, the opportunity is given for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

These and other advantages will become evident from the following more detailed description of the invention.

Problem to be Solved

The general problem to be solved by the present invention is to provide a medicated module, a drug delivery system and a method where the administration of a medicament is facilitated.

SUMMARY

In specific embodiments, our invention allows complex combinations of multiple drug compounds within a single drug delivery system. In particular, a user may be enabled to set and dispense a multi-drug compound device through one single dose setting mechanism and a single dispense interface. This single dose setter may control the mechanism of the device such that a predefined combination of the individual drug compounds or medicaments is delivered when a single dose of one of the medicaments is set and dispensed through the single dispense interface. The term drug dispense interface preferably is, in the context of this disclosure, any type of outlet that allows the two or more medicaments to exit the drug delivery system and be delivered to the patient. In a preferred embodiment the single drug dispense interface comprises a hollow needle cannula.

By defining the therapeutic relationship between the individual drug compounds our delivery device may help ensure that a patient/user receives the optimum therapeutic combination dose from a multi-drug compound device without the inherent risks associated with multiple inputs where the user has to calculate and set the correct dose combination every time they use the device. The combination of the individual medicaments comprises preferably at least two different drug agents, wherein each medicament comprises at least one drug agent. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect, the present application may be of particular benefit to users with dexterity or computational difficulties as the single input and associated predefined therapeutic profile may remove the need for them to calculate their prescribed dose every time they use the device and the single input may allow considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. When connected to the primary device the secondary medicament is activated/delivered on dispense of the primary medicament. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

In one embodiment, our invention relates to a medicated module attachable to a drug delivery device, for example a single dose or multi-dose drug delivery device. Preferably, the medicated module contains a liquid medicament. The medicated module may contain a GLP 1. The medicated module comprises a housing having a proximal end and a distal end, where the proximal end has a connector configured for attachment to a drug delivery device. The drug delivery device may house a primary reservoir containing at least one dose of a first medicament. The primary reservoir may contain multiple doses of the first medicament. The medicated module comprises a reservoir, in the following also called secondary reservoir, containing at least one dose of a medicament. The reservoir may contain only a single dose of the medicament. The medicated module may comprise a containment or reservoir of a secondary medicament within a needle sub-assembly.

By drug delivery device as used herein it is meant to cover traditional syringes, pen-type devices, pumps, osmotic injectors, and the like devices. By user settable dose it is meant dose that the user (patient or health care provider) can physically manipulate the device to set a desired dose of the primary or first medicament. Likewise, the user settable dose can be set remotely through the use of wireless communication (Bluetooth, WiFi, satellite, etc.) or the dose could be set by another integrated device, such as a blood glucose monitor after performing a therapeutic treatment algorithm.

The drug delivery device may comprise a primary reservoir of medicament containing at least one drug agent, a dose setter, a dose button, and a delivery mechanism. The dose button is operably connected to the primary reservoir. The dose setter is operably connected to the primary reservoir. The delivery mechanism may be of any type utilizing a rotatable piston rod, preferably a rotatable piston rod with two distinct threads.

In one embodiment, the medicated module has a double-ended needle fixed within the housing, where the needle has a section that defines a second reservoir. In particular, the section may be an enlarged section between the two ends. The second reservoir preferably contains a single dose of a second medicament. Preferably, one end of the needle is configured for fluid communication with the primary reservoir when the medicated module is attached to the drug delivery device.

In a further embodiment, the medicated module has a first needle fixed within a hub in the proximal end of the housing and a second needle fixed within the distal end of the housing. A recess may be located within the housing that defines the reservoir that is in fluid communication with the second needle.

In another embodiment the medicated module has a housing having a proximal end and a distal end, where the proximal end has a connector configured for attachment to a drug delivery device that has a primary reservoir containing a single or multiple doses of a first medicament. A first needle is fixed within a seal in the proximal end of the housing and a second needle is fixed within the distal end of the housing. A recess is located within the housing that defines a second reservoir that is in fluid communication with the second needle and the seal. The recess may contain a single dose of a second medicament. The first needle is configured for fluid communication with the primary reservoir when the medicated module is attached to the drug delivery device.

In yet another embodiment the medicated module has a first needle fixed within a retention cap inside the module housing and a second needle fixed within the distal end of the housing. The reservoir may be defined by a recess located within the housing. In particular, the reservoir may be located beneath the retention cap and be in fluid communication with the first and second needles. The reservoir may have top and bottom seals configured for fluid engagement with the first and second needles.

In a preferred configuration the secondary reservoir could have a manifold comprising a fluid flow path with reduced cross-sectional area. In a preferred configuration the flow path has an approximately constant cross-sectional area where the axial length is less than the path length due to changing direction of path in at least one plane. One way to accomplish this configuration is through the use of one or more spiral manifolds. To accomplish this, the reservoir may contain at least one spiral manifold that contains a single dose of a second medicament. In a more preferred embodiment, the second reservoir contains two or more spiral manifolds positioned in a stacked arrangement.

Yet another embodiment covers a medicated module where a first needle is fixed within a retention cap positioned in the proximal end of the housing. A second needle is fixed within the distal end of the housing. A second reservoir having top and bottom seals that are configured for fluid engagement with the first and second needles contains a single dose of a second medicament. The medicated module retention cap has retention features engaging the second reservoir. In a more preferred embodiment, the first and second needles pierce the top and bottom seals, respectively, when the medicated module is attached to the drug delivery device. Preferably, the second reservoir is aseptically sealed in a separate container or capsule. The retention cap is preferably configured to move axially in the distal direction when the medicated module is attached to the drug delivery device.

In some cases, where priming of the drug delivery system is desirable, the medicated module has a bypass to allow medicament from the primary reservoir to flow around the secondary reservoir and exit the second needle. The bypass can be any configuration, such as, a channel, pipe, conduit, groove, slot, or any other like pathway that is capable of carrying the medicament from the primary reservoir to the second needle without communicating with the secondary reservoir/medicament. The advantage of such a bypass allows the multi use device to be primed and also both the primary and secondary needles to be primed without expelling any of the volume of the secondary medicament. In this case, the seals of the secondary reservoir may be pierced after priming to allow injection of both the primary and secondary medicament. Alternatively, the bypass channel may be used to inject only the primary medicament. One preferred configuration of the bypass comprises a channel or a groove in the module housing that allows medicament from the primary reservoir to flow around a capsule or contained reservoir containing the second medicament.

Moreover, a method of dispensing at least two medicaments from separate reservoirs is disclosed. The method comprises the steps of first providing a drug delivery device comprising a device housing containing a dose button operably connected to a primary reservoir of medicament containing at least one drug agent. The housing may contain a single dose setter operably connected to a primary reservoir of medicament containing at least one drug agent. Moreover, the drug delivery device comprises a dose button operably connected to the primary reservoir of medicament and a single dispense interface configured for fluid communication with the primary reservoir. Next, the method involves the step of providing a secondary reservoir of medicament containing at least one drug agent configured for fluid communication to the single dispense interface. A single activation of the dose button causes medicament from the primary reservoir and a non-user settable dose of medicament from the secondary reservoir to be expelled through the single dispense interface.

In particular, by using the method, a fixed dose of one medicament and a variable dose of a primary medicament from separate reservoirs may be dispensed. Here, the method may involve the steps of first setting a dose of a first medicament contained in a primary reservoir a drug delivery device having a single dose setter. Next a dose button is activated that moves the set dose of the first medicament from the primary reservoir in a distal direction and simultaneously forcing substantially all of a non-user settable dose (e.g. a single dose) of a second medicament from a secondary reservoir contained in a medicated module, such as those previously described, through a single dispense interface, preferably a hollow injection needle. The method of delivery of the medicaments could be simultaneous or sequential. Upon completion of the delivery procedure substantially all of the second medicament has been expelled as well as the set dose of the first medicament through the single dispense interface. By "substantially all" we mean that at least about 80% of the second medicament is expelled from the drug delivery device, preferably at least about 90% is expelled. In one arrangement, preferably at least about 80% is delivered.

Furthermore, a drug delivery system to deliver two or more medicaments is disclosed, wherein the drug delivery system is operable through a single dispense interface. The drug delivery system comprises a primary reservoir of medicament containing at least one drug agent. In particular, the drug agent of the primary reservoir of medicament may comprise insulin. Furthermore, the drug delivery system may comprise a housing having a single dose setter operably connected to the primary reservoir of medicament. Preferably, by activating the dose button, a user can select the size of a dose of medicament from the primary reservoir. The drug delivery device comprises a dose button operably connected to the primary reservoir of medicament and a single dispense interface configured for fluid communication with the primary reservoir. Furthermore, the drug delivery device comprises a medicated module containing a secondary reservoir of medicament comprising at least one drug agent. The drug agent in the secondary reservoir of medicament may comprise a GLP-1. The secondary reservoir may contain only a single dose of the medicament. A single activation of the dose button causes medicament from the primary reservoir and from the secondary reservoir to be expelled through the drug dispense interface.

In yet another embodiment, our invention is directed to an injection device where the containment of a secondary drug compound is within a needle sub-assembly (medicated module) designed for attachment to an associated primary or master delivery device. The actuation of the master device actuates the dispense of the secondary compound and a primary compound contained in a reservoir in the master drug delivery device. The combination of compounds as discrete units or as a mixed unit is delivered to the body via an integral needle. This would provide a combination drug injection system that, from a user's perspective, would be achieved in a manner that very closely matches the currently available injection devices that use standard needles. One possible delivery procedure would involve the following steps:

1. Attach the medicated needle module to the distal end of the primary injection device (e.g. a threaded hub of a cartridge holder containing a 3 ml cartridge of the primary drug compound) such that the proximal end of the medicated needle is in fluidic communication with the primary compound.
2. Dial up/set the primary injection device such that it is ready to dispense the desired dose of the primary compound.
3. Insert the distal end of the medicated needle into the desired injection site. In some designs, insertion of the medicated needle can trigger delivery of the secondary compound.
4. Dose the primary compound by activating a dose button. This may also cause the secondary compound to automatically dispense.
5. Remove and dispose of the medicated needle module.

The medicated module of our invention can be designed for use with any drug delivery device with an appropriate compatible interface. However, it may be preferable to design the module in such a way as to limit its use to one exclusive primary drug delivery device through employment of dedicated or coded features to prevent attachment of a non-appropriate medicated module to a non-matching injection device. In some situations it may be beneficial from a therapeutic and safety point of view to ensure that the medicated module is exclusive to one drug delivery device (or family of devices) while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting (i.e. delivering the complete dose of the primary therapy in two separate injections) or top-up of the primary compound in a way that would prevent the potential risk of double dosing of the secondary compound.

A particular benefit of specific embodiments of our invention is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a user could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of our invention, the primary drug delivery device is used more than once and therefore is multi-use. Such a device may or may not have a replaceable reservoir of the primary drug compound, but our invention is equally applicable to both scenarios. It is also possible to have a suite of different medicated modules for various conditions that could be prescribed as one-off extra medication to patients already using a standard drug delivery device. Should the user attempt to reuse a previously used medicated module, our invention could include features that could alert the user to this situation. Such means of alerting the user may include some (or all) of the following:
1. Physical prevention of medicated module re-attachment to the primary drug deliver device once the module has been used and removed.
2. Physical prevention of insertion of the used drug dispense interface into the patient (e.g. a single use needle-guard type arrangement).
3. Physical/hydraulic prevention of subsequent liquid flow through the drug dispense interface once it has been used/inserted.
4. Physical locking of the dose setter and/or dose button of the drug delivery device.
5. Visual warnings (e.g. change in color and/or warning text/indicia within an indication window on the module once insertion and/or fluid flow has occurred).
6. Tactile feedback (presence or absence of tactile features on the outer surface of the module hub following use).

A further feature of this embodiment may be that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties. The use of one injection instead of two reduces the possibility for user errors and so may increase patient safety.

A further aspect of the invention relates to a method of delivering two medicaments stored in separate primary packages. The medicaments may both be liquid, or alternatively one or more of the medicaments may be a powder, suspension or slurry. In one embodiment the medicated module could be filled with a powdered or solid tablet of medicament that is either dissolved or entrained in the primary medicament as it is injected through the medicated module.

These, as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
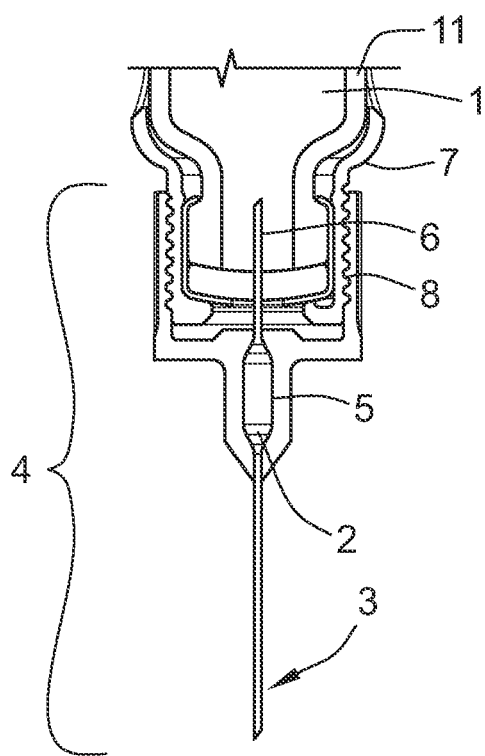
FIG. 1 illustrates an embodiment of the medicated module of the present invention having an enlarged needle portion attached to a drug delivery device.
Figure 2:
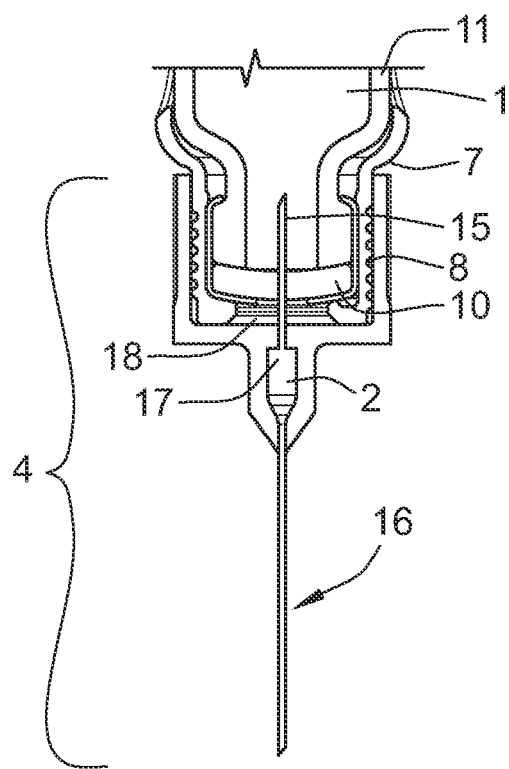
FIG. 2 illustrates an embodiment of the medicated module of the present invention having two needles connected to a secondary reservoir attached to a drug delivery device.
Figure 3:
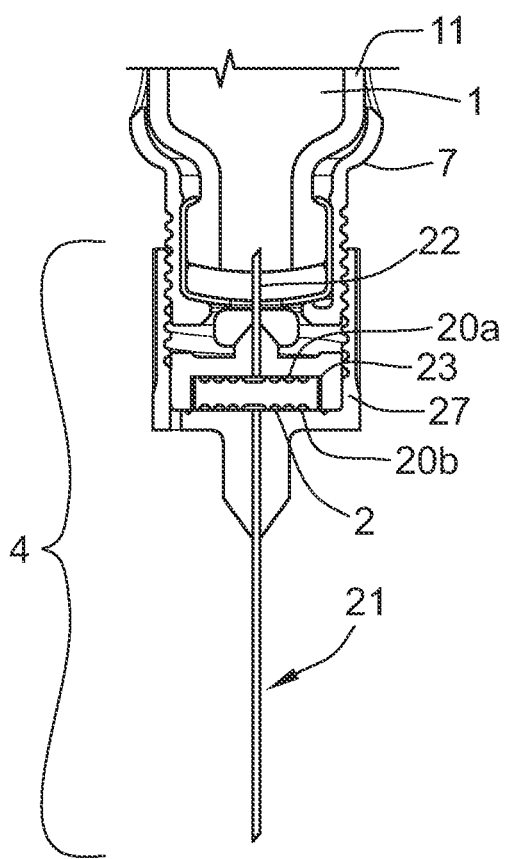
FIG. 3 illustrates an embodiment of the medicated module of the present invention having one or more spiral manifolds as part of the secondary reservoir attached to a drug delivery device.

Specific embodiments of the disclosed drug delivery device enable administering a fixed predetermined dose of a second medicament (secondary drug compound) and a variable dose of a first medicament (primary drug compound) through a single output or drug dispense interface. Setting the dose of the primary medicament by the user may automatically determine the fixed dose of the second medicament, which preferably is a single dose. In a preferred embodiment the drug dispense interface is a needle cannula (hollow needle). FIGS. 1-3 illustrate three different embodiments of our invention, each having a medicated module 4 attached to a drug delivery device 7. Each module is preferably self-contained and provided as a sealed and sterile disposable module that has an attachment means 8 compatible to the attachment means 9 at the distal end of device 7. Although not shown, the medicated module could be supplied by a manufacturer contained in a protective and sterile container where the user would peel or rip open a seal or the container itself to gain access to the sterile medicated module. In some instances it might be desirable to provide two or more seals for each end of the medicated module. The seal may allow display of information required by regulatory labeling requirements.

Figure 8:
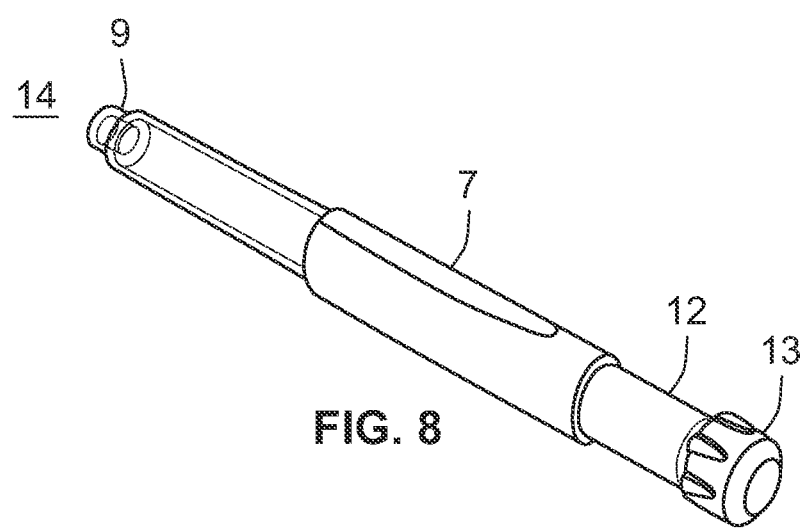
FIG. 8 illustrates one possible drug delivery device that can be used with the present invention.

One example of a drug delivery device 7 is illustrated in FIG. 8. Any known attachment means can be used, including permanent and removable connection means. Threads, snap locks, snap fits, luer locks, bayonet, snap rings, keyed slots, and combinations of such connections can be used to attach module 4 to device 7. FIGS. 1-3 illustrate the attachment means 8 as screw threads. The embodiments shown in FIGS. 1-3 have the benefit of the second medicament 2 as a single dose being contained entirely within the cannula 3, hence minimizing the risk of material incompatibility between the second medicament and the materials used in the construction of the medicated module 4.

As shown in FIG. 1 a unique aspect of this embodiment is the method of construction of output needle 3, part of which has an enlarged cross-section 5 to accommodate the volume of the fixed (single) non-user settable dose medicament 2. Preferably a hydroforming or a swaging process will be utilized to form the enlarged cross-section 5 of the needle 3. Both tips of the needle are preferably not enlarged which is beneficial because it helps minimize both the physical and mental/emotional trauma associated with insertion of larger bore needles as well as minimizing the risk of compromising the sealing integrity of the septa of the primary medicament container (multiple piercing of this type of material with a relatively large gauge needle increases the risk of "coring" of the septum).

To minimize the residual volume of the second medicament that might remain in the needle module or sub-assembly 4 at the end of the dispense operation caused by recirculation, the enlarged section 5 should be designed with fluid flow characterizing models. Preferably, the design of the medicated module 4 should ensure that at least about 80% of the second medicament is expelled through the distal end of needle 3, most preferably at least about 90% should be expelled. Ideally displacement of the first medicament 1 into the proximal end 6 of needle 3 will displace the second medicament 2 without substantial mixing of the two medicaments. Preferably this is accomplished by minimizing the diametric increase and careful design of the transition from the small cross sections of the needle 3 to the enlarged cross section 5. One alternative is to have the assembly/filling process set up so as to ensure that a "plug" of gas (e.g. air or an inert gas such as nitrogen) is present in the upper section 6 of the needle (above the enlarged section 5) this may act to ensure that the first and second medicaments are kept separate from each other thereby help ensure sequential delivery by action of a virtual piston created by the plug of air. This plug may additionally help ensure that there is no opportunity for the primary and secondary medicaments to mix prior to injection (i.e. if the medicated module is left in the attached position for an extended period of time prior to the injection action being undertaken.

Attachment of the medicated module 4 to the multi-use drug delivery device 7 causes the engagement needle 6 located in the module to penetrate the septum 10 of cartridge 11 of the multi-use device 7. Once the engagement needle has passed through the septum of the cartridge fluid connection is made between the first medicament 1 and the output needle 3. The dose of the multi-use drug delivery device 7 is then set using a dose setter 12 (see FIG. 8) in the normal manner (e.g. by dialing out the appropriate number of units). Dispense of the medicaments is then achieved by subcutaneously injecting the medicaments via activation of a dose button 13 on device 7. The dose button of our invention can be any triggering mechanism that causes the dose of the first medicament that was set by the dose setter to move distally towards the distal end 14 of the device. In a preferred embodiment the dose button is operably connected to a spindle that engages a piston in the primary reservoir of the first medicament. In a further embodiment the spindle is a rotatable piston rod comprising two distinct threads.

Another embodiment of our invention is shown in FIG. 2 where a primary needle 15 pierces the septum 10 of the device cartridge 11 and a second needle 16 is used to subcutaneously inject the medicament. Located between the two needles is a recess 17 containing the secondary reservoir of the second medicament. The primary needle 15 is attached to a retention cap 18, which when inserted into the top of the recess 17 provides a fluid seal.

In another embodiment of our invention the secondary reservoir could have a fluid flow path with approximately constant cross-sectional area where the axial length is less than path length due to changing direction of path in at least one plane. One way to accomplish this configuration is through the use of one or more spiral manifolds 20 that are used as part of the secondary reservoir to store the second medicament and to minimize the risk of mixing occurring between the two medicaments during dispense. In minimizing the risk of mixing it is desirable to minimize the cross-sectional area perpendicular to the flow direction where the two medicaments come into contact with each other. While desirable to minimize the cross-sectional area of the flow channel, the effect of this in a standard needle arrangement would be to increase the length of the flow channel for a fixed volume of the second medicament. This can result in an excessive and unacceptable axial length of the medicated module. Using one or more spiral manifolds provides a fluid path of minimal cross-sectional area and sufficient length to store the second medicament, within an acceptable minimum axial package space.

Figure 4:
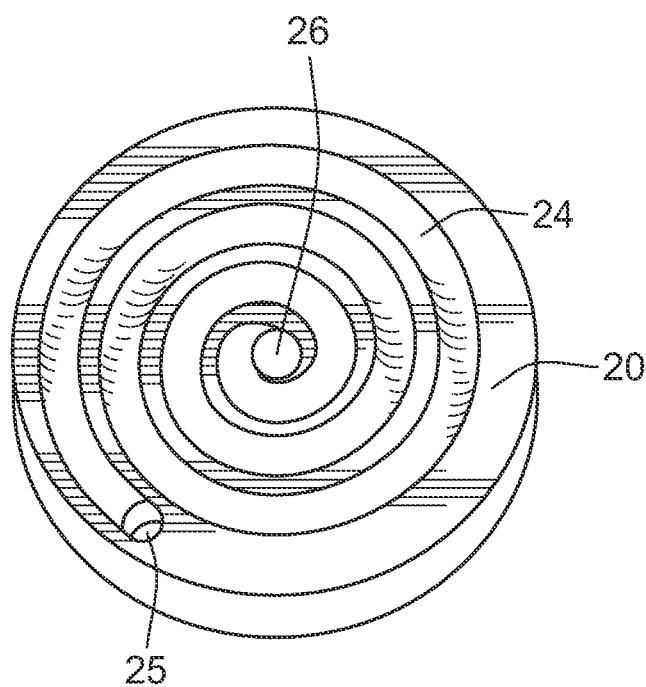
FIG. 4 illustrates a perspective view of an embodiment of one the spiral manifolds that make up part of the secondary reservoir attached to a drug delivery device.

Turning to FIG. 3, two spiral manifolds 20a & 20b (see FIG. 4) are utilized between the cartridge 11 of the reusable device 7 and the output needle 21 to further reduce the axial package space of medicated module 4. The primary needle 22 attaches to a retention cap 23, which introduces the first medicament 1 to the center 26 of the first spiral manifold 20a. As the first medicament is dispensed into spiral manifold 20a, the second medicament 2 flows radially outward along the path of the spiral groove 24 until it reaches a predetermined radial position 25 whereby the flow path traverses through the first spiral manifold. Having passed through the spiral manifold the fluid path follows a second spiral orientated such that the fluid flows radially inward on the second spiral manifold 20b. As the fluid reaches the center of the second spiral manifold 20b fluid communication is made with the output needle 21 and the medicament is dispensed through the outlet needle to the patient.

In this embodiment it is anticipated that the spiral manifolds will have sealing features along the external edges of helical groove (not shown) and/or be made from a compliant material such as rubber, TPE, or like materials, and that the assembly of the retention cap 23 into the body or housing 27 of the medicated module will exploit these features to create a sealing labyrinth, thereby forming the helical flow channel.

Figure 5:
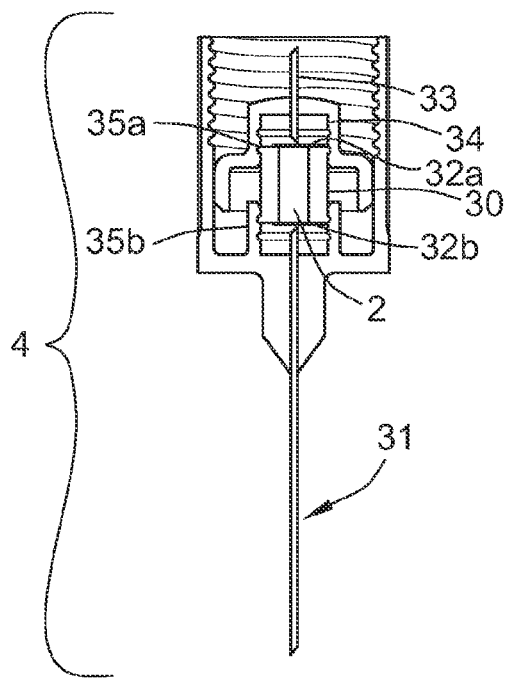
FIG. 5 illustrates an embodiment of the medicated module of the present invention having a self-contained reservoir of secondary medicament having two pierceable membranes.
Figure 6:
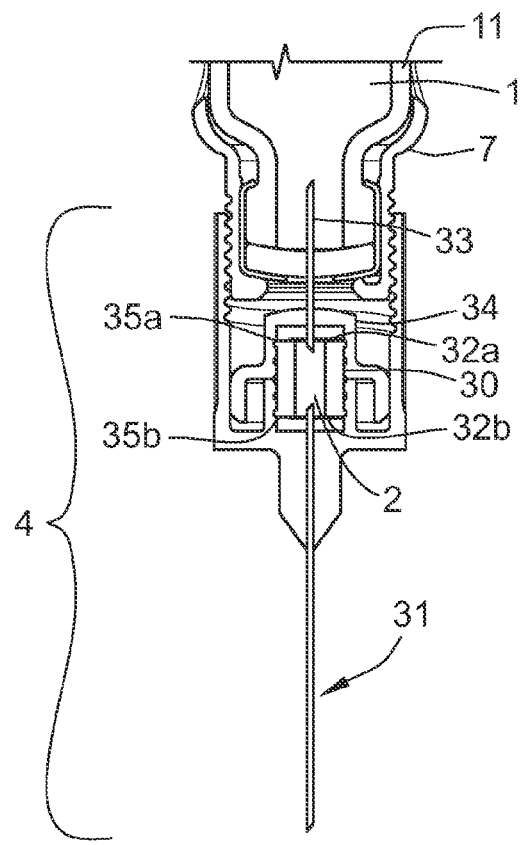
FIG. 6 illustrates an embodiment of the medicated module of the present invention having a self contained reservoir of secondary medicament having two pierceable membranes attached to a delivery device.
Figure 7:
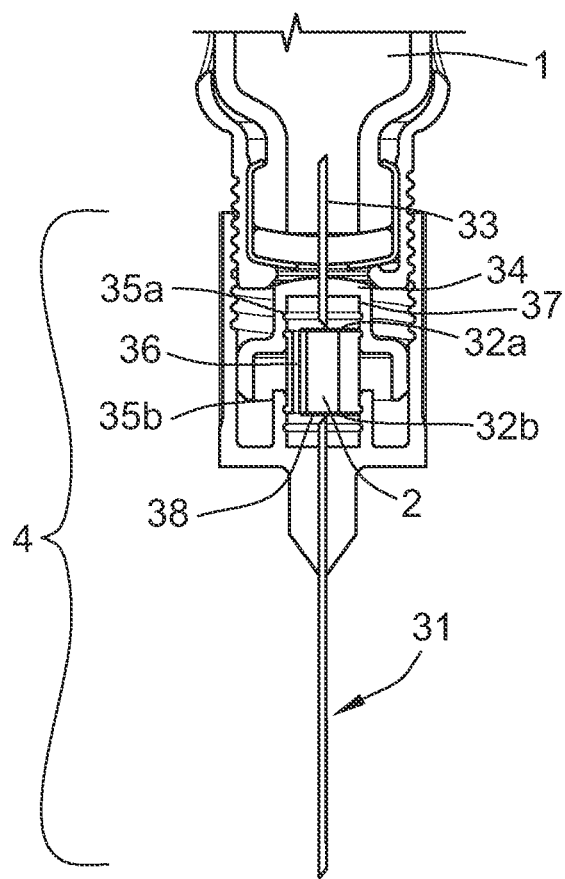
FIG. 7 illustrates an embodiment of the medicated module of the present invention having a self contained reservoir of secondary medicament having two pierceable membranes and a bypass channel attached to a delivery device in priming position.

Additional embodiments of our invention are illustrated in FIGS. 5, 6 & 7. In these embodiments the medicated module 4 contains a discrete secondary reservoir 30 containing a fixed single dose of the second medicament 2. As with the above embodiments these medicated modules administer a fixed predetermined dose of a second medicament and a variable dose of a primary medicament through a single output needle 31. As discussed in more detail below, FIG. 7 shows an alternative design of these embodiments that provides a by-pass feature preferably used for priming using the primary medicament 1.

In the embodiments shown in FIGS. 5-7 reservoir 30 has ends that are sealed with pierceable membranes 32a and 32b that provide a hermetically sealed reservoir for the second medicament. A primary needle 33 can be displaced axially relative to the reservoir 30 such that in a depressed position the primary needle 33 will puncture the top membrane 32a. The output needle 31 protrudes above the lower surface of reservoir 30 and pierces the lower membrane 32b when the reservoir is moved axially relative to needle 31.

During use, on attachment of the medicated module to a multi-use device, such as the one shown in FIG. 8, the primary needle 33 pierces septum 10 of cartridge 11 contained in the drug delivery device 7. This attachment causes the retention cap 34 to move distally a predetermined axial displacement so that the retention cap 34 bears against the cartridge causing the retention features 35a and 35b to be overcome and the primary needle to pierce the top membrane 32a of reservoir 30. Once the top of the reservoir bears against the retention cap the retention features holding the reservoir in the medicated module 4 are overcome and the reservoir moves axially downward. Axial movement of reservoir 30 causes the proximal end of output needle 31 to pierce lower membrane 32b of reservoir 30.

In any of the above described embodiments of our invention the second medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

Yet another embodiment of our invention is shown in FIG. 7 where a bypass channel 36 is incorporated into reservoir 30 to preferably facilitate priming of output needle 31 with the first medicament 1, and/or priming of the mechanism within the device 7. During attachment of the medicated module 4 of this embodiment to a device, such as the one shown in FIG. 8, the primary needle 33 starts to pierce septum 32a of reservoir 30. However, prior to the primary needle piercing the membrane the user has the option of initiating a priming operation utilizing bypass channel 36. This is achieved by dispensing the primary medicament into the cavity 37 between the retention cap 34 and the top pierceable membrane 32a. Since the cavity 37 is in fluid communication with bypass channel 36, the primary medicament flows around reservoir 30 and into lower cavity 38 and out through output needle 31. After the optional priming operation is complete the medicated module can be fully attached (rotated in the case of screw threads) to the multi-use device 7 causing the output and primary needles to pierce the lower and top membranes of the reservoir, respectively. Piercing of membranes 32a and 32b opens fluid communication between the first and second medicaments allowing them to be dispensed through operation of the dispense mechanism on the multi-use device. When this occurs, bypass channel 36 and cavities 37 and 38 are isolated from the contents of reservoir 30. To allow the assembly to move axially downward fully into the "ready to use" state (as illustrated in FIG. 6) features may be present in the invention to ensure that any primary medicament in cavities 37 or 38 during this final attachment operation is either expelled into the output needle, or safely contained in a separate region of the medicated module that is not in fluid communication with the outlet needle during use. Differentiation between the priming and fully attached states of the medicated module relative to the multi-use device could be achieved by though indicators such as tactile, audible, visual and the like design features.

The connection or attachment between the medicated module of the above described embodiments may contain additional features (not shown), such as connectors, stops, splines, ribs, grooves, pips, clips and the like design features, that ensure that specific medicated modules are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the secondary medicament and for attaching one or more needle cannula. The secondary reservoir can be manufactured from glass or other drug contact suitable material. The integrated injection needle can be any needle cannula suitable for subcutaneous or intramuscular injection. Additionally, the medicated module could incorporate a safety shield device that would prevent accidental needle sticks and reduces the anxiety experienced by users who suffer from needle phobia. The exact design of the safety shield is not critical to our invention, however, a preferred design is one that is operably connected to the first and/or second reservoirs. In such a design the activation of the safety shield could unlock the drug delivery system or instigate fluid communication between the reservoirs and in some cases cause the second medicament to be dispensed prior to activating the dose button to dispense the primary medicament from the first reservoir.

Preferably the medicated module is provided by a manufacture as a stand-alone and separate device that is sealed to preserve sterility. The sterile seal of the module is preferably designed to be opened automatically, e.g. by cutting, tearing or peeling, when the medicated module is advanced or attached to the drug delivery device by the user. This opening of the seal may be assisted by features such as angled surfaces on the end of the injection device or features inside the module.

The medicated module of our invention may be designed to operate in conjunction with a multiple use injection device, preferably a pen-type multi-dose injection device, similar to what is illustrated in FIG. 8. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose, but in either case it is a multi-dose device.

A typical injection device contains a cartridge or other reservoir of medication. This cartridge is typically cylindrical in shape and is usually manufactured in glass. The cartridge is sealed at one end with a rubber bung and at the other end by a rubber septum. The injection pen is designed to deliver multiple injections. The delivery mechanism is typically powered by a manual action of the user, however, the injection mechanism may also be powered by other means such as a spring, compressed gas or electrical energy.

In certain embodiments where the medicated module contains a single dose of a medicament, the module may have to be attached to a drug delivery device in order to administer the single dose in the reservoir to a patient. In other words, the medicated module may not be configured to be used as a stand-alone injection device. This is because the module does not have a dose delivery mechanism and instead relies on the dose delivery mechanism contained in the drug delivery device to which it must be attached.

Exemplary embodiments of the present invention have been described. Those skilled in the art will understand, however, that changes and modifications may be made to these embodiments without departing from the true scope and spirit of the present invention, which is defined by the claims.

LIST OF REFERENCES 1 first medicament
2 second medicament
3 needle
4 medicated module/assembly
5 enlarged cross-section
6 section of needle/engagement needle
7 drug delivery device
8 attachment means
9 attachment means of the drug delivery device
10 septum
11 cartridge
12 dose setter
13 dose button
14 distal end of device
15 primary needle
16 second needle
17 recess
18 retention cap
20, 20a, 20b spiral manifolds
21 output needle
22 primary needle
23 retention cap
24 spiral groove
25 radial position
26 center of spiral manifold
27 body/housing of medicated module
30 secondary reservoir
31 output needle
32a, 32b pierceable membrane/septum/seal
33 primary needle
34 retention cap
35a, 35b retention features
36 bypass channel
37 cavity
38 lower cavity

We claim:

1. A medicated module attachable to a drug delivery device, comprising,
 a. a housing having a proximal end and a distal end, where the proximal end has a connector configured for attachment to a drug delivery device;
 b. a reservoir containing at least one dose of a medicament
 c. a first needle fixed within a hub in the proximal end of the housing or fixed within a retention cap inside the housing;
 d. a second needle fixed within the distal end of the housing wherein the reservoir is located between the first needle and the second needle; and
 wherein the reservoir has top and bottom seals configured for fluid engagement with the first and second needles.

2. A medicated module attachable to a drug delivery device, comprising,
 a. a housing having a proximal end and a distal end, where the proximal end has a connector configured for attachment to a drug delivery device;
 b. a reservoir containing at least one dose of a medicament
 c. a first needle fixed within a hub in the proximal end of the housing or fixed within a retention cap inside the housing;
 d. a second needle fixed within the distal end of the housing wherein the reservoir is located between the first needle and the second needle; and
 a. a recess within the housing that defines the reservoir that is in fluid communication with the second needle.

3. The medicated module of claim 2, further comprising,
 a. a recess within the housing and beneath the retention cap that defines the reservoir that is in fluid communication with the first and second needles.

4. The medicated module of claim 1 where the reservoir contains a single dose of the medicament.

5. The medicated module of claim 1 where at least one manifold is positioned in the reservoir.

6. The medicated module of claim 5 where a single dose of the medicament is contained in the manifold.

7. The medicated module of claim 5 where a second manifold is in a stacked position with the at least one manifold.

8. The medicated module of claim 1 where the retention cap has retention features engaging the reservoir.

9. The medicated module of claim 1 wherein the first and second needles pierce the top and bottom seals, respectively, when the medicated module is attached to a drug delivery device or upon activation by a user.

10. The medicated module of claim 1 where the retention cap is configured to move axially in the distal direction relative to the medicated module when the medicated module is attached to a drug delivery device.

11. The medicated module of claim 1, further comprising a bypass to allow medicament from a primary reservoir to flow through the bypass and exit the second needle.

12. A drug delivery system to deliver two or more medicaments operable through a single dispense interface, comprising,
   a. a primary reservoir of medicament containing at least one drug agent;
   b. a dose button operably connected to the primary reservoir of medicament;
   c. a single dispense interface configured for fluid communication with the primary reservoir; and
   d. a medicated module comprising,
      a housing having a proximal end and a distal end, where the proximal end has a connector configured for attachment to a drug delivery device;
      a reservoir containing at least one dose of a medicament;
      a first needle fixed within a hub in the proximal end of the housing or fixed within a retention cap inside the housing;
      a second needle fixed within the distal end of the housing
   wherein the reservoir has top and bottom seals configured for fluid engagement with the first and second needles, and
   wherein the reservoir is located between the first needle and the second needle
   wherein a single activation of the dose button causes medicament from the primary reservoir and from the secondary reservoir to be expelled through the drug dispense interface.

13. The system of claim 12 where the secondary reservoir contains a single dose of the drug agent.

14. The system of claim 12 where at least one of the primary reservoir and the secondary reservoir contains a liquid medicament.

* * * * *